United States Patent [19]

Wendel et al.

[11] Patent Number: 5,380,760
[45] Date of Patent: Jan. 10, 1995

[54] TRANSDERMAL PROSTAGLANDIN COMPOSITION

[75] Inventors: Hanns Wendel; Franz-Josef Braun, both of Borken, Germany

[73] Assignee: Minnesota Mining and Manufacturing Company, St. Paul, Minn.

[21] Appl. No.: 155,126

[22] Filed: Nov. 19, 1993

[51] Int. Cl.⁶ ............................................. A61K 31/19
[52] U.S. Cl. ................................................... 514/573
[58] Field of Search ........................................ 514/573

[56] References Cited

U.S. PATENT DOCUMENTS

| | | | |
|---|---|---|---|
| 3,069,322 | 12/1962 | Bergstrom et al. | 167/74 |
| 4,103,026 | 7/1978 | Carlson | 424/305 |
| 4,254,145 | 3/1981 | Birnbaum et al. | 514/573 |
| 4,515,810 | 5/1985 | Chow et al. | 514/530 |
| 4,594,240 | 6/1986 | Kawata et al. | 424/28 |
| 4,707,495 | 11/1987 | Rosenthale et al. | 514/573 |
| 4,889,845 | 12/1989 | Ritter et al. | 514/63 |
| 5,219,885 | 6/1993 | Frolich et al. | 514/530 |

FOREIGN PATENT DOCUMENTS

| | | |
|---|---|---|
| 1308027 | 9/1992 | Canada. |
| 63-135333 | 6/1988 | Japan. |
| 2-264725 | 10/1990 | Japan. |

OTHER PUBLICATIONS

J. Org. Chem. 1974, 37, 2921.
J. Chromatography, 1991, 555, 73.

*Primary Examiner*—Johann Richter
*Assistant Examiner*—John Peabody
*Attorney, Agent, or Firm*—Gary L. Griswold; Walter N. Kirn; Douglas E. Reedich

[57] ABSTRACT

Transdermal drug formulations containing a prostaglandin, optionally a lipophilic excipient, and a polyisobutylene pressure sensitive adhesive.

10 Claims, 1 Drawing Sheet

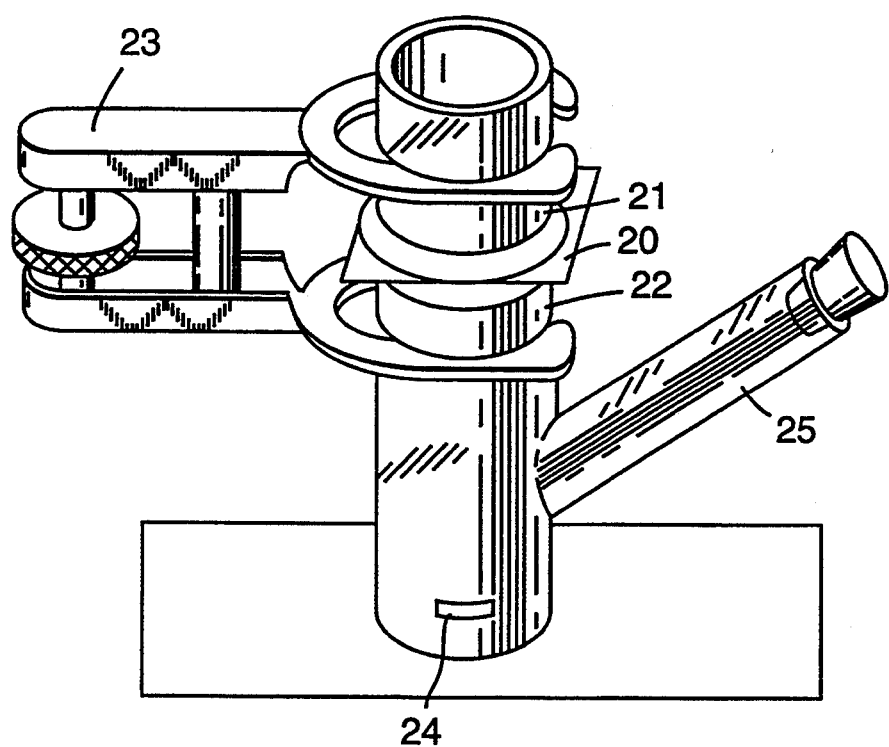

TRANSDERMAL PROSTAGLANDIN COMPOSITION

BACKGROUND OF THE INVENTION

1. Field of the Invention

This invention relates to topical and transdermal drug formulations. In another aspect this invention relates to formulations containing prostaglandins or derivatives thereof, particularly prostaglandin $E_1$ esters.

2. Description of the Related Art

Topical and transdermal drug formulations are designed to deliver a therapeutically effective amount of drug to or across the skin of a patient. Devices known to the art include reservoir type devices involving membranes that control the rate of drug release to the skin, gels and creams, and devices involving a dispersion of the drug in a matrix such as a pressure sensitive adhesive. As the skin presents a barrier to the drug it is often desirable or necessary to incorporate certain materials that enhance the rate at which the drug passes through the skin. For any particular drug, however, the type of device, the transdermal flux rate that is suitable, and suitable formulation components, are dependent upon the particular drug to be delivered.

Prostaglandins as a class of compounds have diverse pharmacologic activity, including stimulation of gastrointestinal and reproductive smooth muscle, relaxation and contraction of respiratory smooth muscle, hypotensive activity, inhibition of fatty acid lipolysis, inhibition of blood platelet aggregation, and inhibition of gastric acid secretion. Therapeutic utility of prostaglandins in general is correspondingly broad. As for prostaglandin $E_1$ ("$PGE_1$")in particular, this compound, salts thereof, and lower alkyl esters thereof are well known and disclosed, e.g., in U.S. Pat. Nos. 3,069,322 (Bergstrom et al.), 5,219,885 (Froelich et al.) and in J. Org. Chem. 1974, 37, 2921. $PGE_1$ has found utility in the treatment of peripheral occlusive diseases, acute myocardial infarction, angina pectoris, acute ischaemic stroke, asthma, gastrointestinal ulcers, ulcers of the skin, and organ rejection. Various routes of administration have been described, including oral, intravenous, buccal, rectal, intraarterial, subcutaneous, and sublingual. The preferred route of administration of $PGE_1$ will of course be dependent on the particular intended therapeutic use.

Topical and transdermal administration of $PGE_1$ and $PGE_1$ derivatives have also been described, e.g., in U.S. Pat. Nos. 4,889,845 (Ritter et al.), 4,515,810 (Chow et al.), and 5,219,885 (Froelich et al.) and in Japanese Kokai 2-264725 (Morimoto et al.) and 63-135333 (Nakano et al.). In order for a transdermal formulation of $PGE_1$ or a derivative thereof to be effective and suitable it is desirable that the formulation have a high transdermal flux rate, allowing a therapeutically effective blood level of the drug to be achieved or maintained when the formulation is applied to a relatively small area of the skin. Furthermore $PGE_1$ readily undergoes certain reactions and rearrangements (see. e.g., J. Chromatography, 1991, 555, 73 (Lee et al.). This instability of the prostaglandin can be problematic in providing a suitable transdermal formulation.

SUMMARY OF THE INVENTION

This invention provides a pressure sensitive adhesive topical and/or transdermal drug delivery formulation, comprising:

(i) a therapeutically effective amount of prostaglandin $E_1$ or a pharmaceutically acceptable salt or lower alkyl ester thereof;

(ii) optionally a skin penetration enhancing amount of an excipient selected from the group consisting of isopropyl myristate, ethyl oleate, and a mixture thereof; and (iii) a polyisobutylene pressure sensitive adhesive, wherein component (i) and, if present, component (ii), are dissolved or substantially uniformly dispersed in the polyisobutylene pressure sensitive adhesive.

This invention also provides an adhesive coated sheet material comprising a flexible backing bearing on one surface thereof a formulation comprising a combination of:

(i) a therapeutically effective amount of prostaglandin $E_1$ or a pharmaceutically acceptable salt or lower alkyl ester thereof;

(ii) optionally a skin penetration enhancing amount of an excipient selected from the group consisting of isopropyl myristate, ethyl oleate, and a mixture thereof; and (iii) a polyisobutylene pressure sensitive adhesive.

This invention also provides a method of treating in an animal a condition capable of treatment by prostaglandin $E_1$ or a pharmaceutically acceptable salt or lower alkyl ester thereof, comprising the steps of:

(i) providing a formulation as described above;

(ii) applying the formulation to the skin of the animal; and (iii) allowing the formulation to remain on the skin in order to establish or maintain a therapeutically effective blood level of prostaglandin $E_1$.

The combination of prostaglandin $E_1$ or a pharmaceutically acceptable salt or lower alkyl ester thereof with the other components defined above has been found to afford particularly high prostaglandin transdermal flux rates. Furthermore the formulations of the invention are stable to prostaglandin decomposition for extended periods of time.

BRIEF DESCRIPTION OF THE DRAWING

The drawing shows a perspective view of a diffusion cell used to determine transdermal flux of a formulation of the invention.

DETAILED DESCRIPTION OF THE INVENTION

The formulations of the invention comprise a combination of a pressure sensitive adhesive, a prostaglandin, and optionally a lipophilic excipient. Preferably the prostaglandin and the optional excipient (if present) are substantially uniformly distributed within and throughout the pressure sensitive adhesive component.

Prostaglandins are well known to those skilled in the art. This class of drugs includes those derivatives of prostanoic acid (5-octylcyclopentaneheptanoic acid) referred to as A-I series prostaglandins. Prostaglandin nomenclature is well known and disclosed, e.g., in page 409, Remington's Pharmaceutical Sciences, 18th Edition, 1990, A. R. Gennaro, Ed., Mack Publishing Company, Easton, Pa. The term "prostaglandin" as used generically herein refers to the prostaglandin free acid and pharmaceutically acceptable derivatives thereof, including salts and esters. Preferred prostaglandins for use in the formulations of this invention include those prostaglandins comprising a $\beta$-hydroxyketone moiety, including D-series and E-series prostaglandins, preferably E-series prostaglandins such as prostaglandin $E_1$, including pharmaceutically acceptable salts and lower alkyl esters thereof (the term "lower alkyl" as used herein means straight chain or branched chain alkyl containing one to four carbon atoms). Most preferred are lower alkyl esters, especially the ethyl ester of prostaglandin $E_1$ (commercially available from Sigma Chemical Company, St. Louis, Mo., and preparable as disclosed, e.g., in U.S. Pat. No. 5,219,885).

The prostaglandin is present in a formulation of the invention in a therapeutically effective amount. The amount that constitutes a therapeutically effective amount varies according to the particular prostaglandin to be delivered, the indication to be treated, the surface area of the skin over which the formulation is to be placed, and on the other components of the formulation. Accordingly it is not practical to enumerate particular preferred amounts but such can be readily determined by those skilled in the art with due consideration of these factors. Generally, however, the prostaglandin is present in an amount of about 0.005 to about 0.5 percent, preferably about 0.005 to about 0.1 percent, by weight based on the total weight of the formulation. The prostaglandin can be dissolved or substantially uniformly dispersed in the formulation. It is preferably soluble (and dissolved) in the formulation.

The formulations of the invention optionally and preferably contain a lipophilic excipient. Suitable lipophilic excipients include fatty acid alkyl esters, preferably alkyl esters of $C_8$–$C_{22}$ fatty acids, more preferably alkyl esters of $C_{12}$–$C_{18}$ fatty acids. Lower alkyl esters such as ethyl oleate, isopropyl palmitate, and isopropyl myristate are preferred. Most preferred lipophilic excipients are selected from the group consisting of ethyl oleate, isopropyl myristate, and mixtures thereof. The excipient is preferably present in an amount effective to enhance penetration of the prostaglandin through the skin when tested according to the In Vitro Test Method described in detail below. The lipophilic excipient preferably constitutes about 0.01 to about 40 percent, more preferably 10 to about 30 percent, most preferably about 25 percent, of the formulation by weight based on the total weight of the formulation.

The formulations of the invention also contain a polyisobutylene pressure sensitive adhesive. The polyisobutylene pressure sensitive adhesive preferably constitutes from about 60 to about 99.995 percent by weight, more preferably about 70 to about 90 percent by weight, and most preferably about 75 percent by weight of the formulation, based on the total weight of the formulation.

The polyisobutylene pressure sensitive adhesive preferably is soft such that the ultimate composition conforms to the skin and can be worn without significant discomfort to the user. Further, it is selected such that a composition of the invention does not exhibit excessive cold-flow when stored at room temperature. Preferred polyisobutylene pressure sensitive adhesives generally comprise a medium molecular weight polyisobutylene (i.e., a polyisobutylene having a viscosity average molecular weight between about 40,000 and about 100,000) in order that the composition possesses sufficient tack for use on the skin. In order to increase properties such as elasticity or tear resistance an elastomeric high molecular weight polyisobutylene (i.e., a polyisobutylene having a viscosity average molecular weight between about 500,000 and about 2,500,000) can be included. Preferred polyisobutylene pressure sensitive adhesives include polyisobutylene mixtures comprising, based on the total weight of the polyisobutylene mixture, from about 10% to about 60% preferably about 30% to about 50%, and most preferably about 40% by weight of a polyisobutylene with a viscosity average molecular weight between about 500,000 and about 2,500,000, preferably about 1,100,000, and from about 40% to about 90%, preferably about 50% to about 80%, and most preferably about 60%, by weight of a polyisobutylene with a viscosity average molecular weight between about 40,000 and about 100,000, preferably about 40,000.

Exemplary specific polyisobutylenes suitable for use in the formulation of the invention include those commercially available from Exxon Chemical Co., Houston Tex., under the trade designation VISTANEX TM polyisobutylene and those commercially available from BASF under the trade designation OPPANOL TM polyisobutylene. Preferred polyisobutylenes include VISTANEX TM LM-MH polyisobutylene (viscosity average molecular weight about 53,000), VISTANEX TM L-80 polyisobutylene (viscosity average molecular weight about 900,000), VISTANEX TM L-100 polyisobutylene (viscosity average molecular weight about 1,250,000), OPPANOL TM B-120 polyisobutylene (viscosity average molecular weight about 1,500,000), OPPANOL TM B-100 polyisobutylene (viscosity average molecular weight about 1,110,000), OPPANOL TM B-80 polyisobutylene (viscosity average molecular weight about 800,000), OPPANOL TM B-10 polyisobutylene (viscosity average molecular weight about 40,000), and OPPANOL TM B-12 polyisobutylene (viscosity average molecular weight about 60,000). Particularly preferred is a pressure sensitive adhesive consisting of about 40% by weight of OPPANOL TM B-100 polyisobutylene and about 60% by weight of OPPANOL TM B-10 polyisobutylene.

Since polyisobutylene pressure sensitive adhesives such as those described above are inherently tacky there is no need to add tackifiers. However, such can be added if desired. It is preferred that the pressure sensitive adhesive contain a stabilizer such as 2,6-di-t-butyl-4-methylphenol (BHT) in an amount (e.g., 100–500 ppm) effective to minimize or prevent free radical induced decomposition of the polyisobutylene. Certain commercially available polyisobutylenes contain such stabilizers.

Adhesive coated sheet materials of the invention can be prepared by combining dry adhesive, drug, and the excipient or excipients with a suitable organic solvent (e.g., hexane, heptane, ethyl acetate, ethanol, or methanol, depending upon the particular adhesive used) to afford a coating solution. The total solids content of the solution is preferably in the range of about 15 percent to about 40 percent, and more preferably in the range of about 20 to about 35 percent by weight, based on the total weight of the coating solution.

The coating solutions described above are preferably coated onto one surface of a suitable backing of sheet material, such as a film, to form a pressure sensitive adhesive coated sheet material. A pressure sensitive adhesive coated sheet material of the invention can be prepared by knife coating a suitable release liner to a predetermined uniform thickness with a wet adhesive formulation. Suitable release liners include conventional release liners comprising a known sheet material, such as a polyester web, a polyethylene web, or a polystyrene web, or polyethylene-coated paper, coated with a suitable silicone-type coating such as that available under the trade designation Daubert 164Z, from Daubert Co. A preferred release liner is SCOTCHPAK brand 1022 film (3M).

The adhesive coated release liner is then dried and laminated onto a backing using conventional methods. The backing can be occlusive, non-occlusive or a breathable film as desired. The backing is flexible such that it conforms to the skin. It can be any of the conventional materials for pressure sensitive adhesive tapes, such as polyethylene, particularly low density polyethylene, linear low density polyethylene, high density polyethylene, randomly-oriented nylon fibers, polypropylene, ethylene-vinylacetate copolymer, polyurethane, rayon and the like. Backings that are layered, such as polyethylene-aluminum-polyethylene composites are also suitable. The backing should be substantially non-reactive with the ingredients of the formulation. A particularly preferred backing is a 0.08 mm (0.003 inch) thick extruded film of an ethylene/vinyl acetate copolymer containing 19% vinyl acetate incorporated (ULTRATHENE UE631-000, Quantum Chemical Corporation Deer Park, Tex.).

The adhesive coated sheet material of the invention can be made in the form of an article such as a tape, a patch, a sheet, a dressing or any other form known to those skilled in the art.

A formulation of the invention can be used to treat any condition capable of treatment with a prostaglandin, e.g., peripheral arterial occlusive disease. The formulation can be placed on the skin and allowed to remain for a time sufficient to achieve or maintain the intended therapeutic effect. Drug delivery can be topical such that the drug has a local therapeutic effect or transdermal such that the drug has a systemic effect.

The examples set forth below are intended to illustrate the invention.

The following test methods have been employed in the examples which thereafter follow.

IN VITRO TEST METHOD

Although animal skins are known to give significant quantitative differences in drug penetrability as compared to human skin, a rank order correlation is generally observed with various drugs (M. J. Bartek and J. A. LaBudde in "Animal Models in Dermatology", H. Maibach, Ed., Churchill Livingstone, N.Y., 1975, pp. 103-119). Hairless mouse skin has been recommended as a readily available animal skin for use in diffusion cells with steroids and other small molecules (R. B. Stoughton, *Arch. Derm.*, 99, 753 (1969), J. L. Cohen and R. B. Stoughton, *J. Invest. Derm.* 62, 507 (1974), R. B. Stoughton in "Animal Models in Dermatology", pp. 121-131). In the specific test procedure used herein, hairless mouse skin removed from female hairless mice that were 5-6 weeks old was used. The skin was maintained on ice until use, and it was preferably used within 8 hours of sacrifice. The mouse skin was mounted on a water jacketed diffusion cell of the general type shown in the Drawing. The cell is modeled after those described in the literature, e.g., J. L. Cohen, R. B. Stoughton, *J. Invest. Derm.*, 62, 507 (1974) and R. B. Stoughton, *Arch. Derm.*, 99, 753 (1964). As shown in the Drawing, mouse skin 20 was mounted epidermal side up between upper portion 21 and lower portion 22 of the cell, which are held together by means of ball joint clamp 23.

The portion of the cell below the mounted skin was completely filled with receptor fluid ("HBSS", Hank's Balanced Salts, Sigma Chemical Company, St. Louis, Mo., pH adjusted to 7 with hydrochloric acid and containing, based on total volume, 30% by volume ethanol and 15% by volume dimethylisosorbide) such that the receptor fluid contacted the skin. The receptor fluid was stirred using magnetic stir bar 24 and a magnetic stirrer (not illustrated). The sampling port 25 was covered except when in use.

When an adhesive coated sheet material was evaluated, the skin was mounted on the diffusion cell and a 1.7 cm$^2$ patch was applied to the skin and pressed to cause uniform contact to the skin. Generally, the formulation was applied to the skin prior to the time the receptor fluid was added to the cell below the skin.

To maintain constant temperature, water at a temperature of 32° C. was circulated through the water jacket of the diffusion cell. The receptor fluid was stirred by means of a magnetic stirrer throughout the experiment to assure a uniform sample and a reduced diffusion barrier layer on the dermal side of the skin. The receptor fluid was replaced at 3, 7, 10, 17, and 24 hours. The withdrawn receptor fluid was analyzed for drug content by conventional high pressure liquid chromatography.

EXAMPLE 1

An adhesive coated sheet material of the invention was prepared as follows:

The excipient (isopropyl myristate, 24.0 g), the prostaglandin (PGE$_1$ ethyl ester, 0.48 g), and the components of a polyisobutylene pressure sensitive adhesive (43.2 g OPPANOL ™ B-10 polyisobutylene and 28.8 g OPPANOL ™ B-100 polyisobutylene) were combined in an appropriate solvent (n-hexane, 228 g) to form a coating solution. The coating solution was knife-coated out onto a transparent release liner (SCOTCHPAK ™ 1022 liner, 3M) at a wet film thickness of 580 μm. The coating was dried for 2 min at 20° C. and then for 60 min at 40° C.

A backing was prepared by extruding a film of an ethylene/vinyl acetate copolymer containing 19% vinyl acetate incorporated (ULTRATHENE UE631-000, Quantum Chemical Corporation Deer Park, Tex.) to a thickness of 0.08 mm (0.003 inch) onto a 0.125 mm (0.005 inch) thick SCOTCHCAL brand SCW 355BS backsize-coated carrier paper (3M).

The coated release liner was laminated onto the backing and the carrier paper was removed. The resulting device had a drug loading of 50 μg/cm$^2$.

An adhesive coated sheet material prepared as described above was tested according to the In Vitro Test Method described above. The cumulative amount of drug released ("CAR") at the various sampling points is given in the Table below, wherein the values stated are the average of 4 independent determinations using a different mouse skin for each determination.

| TIME (h) | 0 | 3 | 7 | 10 | 17 | 24 |
|---|---|---|---|---|---|---|
| CAR (μg/cm$^2$) | 0 | 0.71 ± 0.41 | 2.57 ± 1.98 | 3.41 ± 2.8 | 7.22 ± 3.38 | 10.10 ± 3.68 |

The results in the Table show that the composition of the invention releases the prostaglandin across hairless mouse skin at a relatively constant rate of about 0.45 μg/h/cm$^2$ over a period of 24 hours.

The claimed invention is:

1. A pressure sensitive adhesive topical and/or transdermal drug delivery formulation, comprising:
   (i) a therapeutically effective amount of prostaglandin $E_1$ or a pharmaceutically acceptable salt or lower alkyl ester thereof; and
   (ii) a polyisobutylene pressure sensitive adhesive,
   wherein the prostaglandin is dissolved or substantially uniformly dispersed in the polyisobutylene pressure sensitive adhesive.

2. A formulation according to claim 1, further comprising a skin penetration enhancing amount of an excipient selected from the group consisting of isopropyl myristate, ethyl oleate, and a mixture thereof, dissolved or substantially uniformly dispersed in the polyisobutylene pressure sensitive adhesive.

3. A formulation according to claim 1 wherein the prostaglandin is prostaglandin $E_1$ ethyl ester.

4. A formulation according to claim 1 wherein the prostaglandin is present in an amount of about 0.005 to about 0.5 percent by weight based on the total weight of the formulation.

5. A formulation according to claim 2, wherein the excipient is ethyl oleate.

6. A formulation according to claim 2, wherein the excipient is isopropyl myristate.

7. A formulation according to claim 1 comprising about 60 to about 99.995 percent by weight of the polyisobutylene pressure sensitive adhesive based on the total weight of the formulation.

8. A formulation according to claim 2 comprising about 70 to about 90 percent by weight of the polyisobutylene pressure sensitive adhesive based on the total weight of the formulation.

9. A formulation according to claim 6, wherein the excipient is present in an amount of about 10 to about 30 percent by weight based on the total weight of the formulation.

10. A method of treating a peripheral arterial occlusive disease in an animal by administering prostaglandin $E_1$ or a pharmaceutically acceptable salt or lower alkyl ester thereof, comprising the steps of:
    (i) providing a formulation according to claim 1;
    (ii) applying the formulation to the skin of the animal; and
    (iii) allowing the formulation to remain on the skin in order to establish or maintain a therapeutically effective blood level of prostaglandin $E_1$.

* * * * *